US007544348B2

(12) United States Patent
Jacob et al.

(10) Patent No.: US 7,544,348 B2
(45) Date of Patent: Jun. 9, 2009

(54) LIQUID FORMULATIONS FOR THE PREVENTION AND TREATMENT OF MUCOSAL DISEASES AND DISORDERS

(75) Inventors: Jeremy E. Jacob, Lewisville, TX (US); David P. Nowotnik, Colleyville, TX (US); Christiane M. Baud, Dallas, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 0 days.

(21) Appl. No.: 10/219,634

(22) Filed: Aug. 15, 2002

(65) Prior Publication Data
US 2003/0060486 A1   Mar. 27, 2003

Related U.S. Application Data

(63) Continuation-in-part of application No. 10/077,459, filed on Feb. 15, 2002.

(60) Provisional application No. 60/269,049, filed on Feb. 15, 2001.

(51) Int. Cl.
*A61K 8/00* (2006.01)
*A61K 8/18* (2006.01)
*A61K 47/32* (2006.01)
*A61Q 11/00* (2006.01)

(52) U.S. Cl. ............... 424/49; 424/401; 424/78.18; 424/78.24; 424/78.29; 424/78.31; 424/78.35; 514/772.1; 514/772.5; 514/772.6; 514/772.7; 514/780; 514/781; 514/782; 514/901

(58) Field of Classification Search ............... 514/772, 514/772.1, 772.2, 772.3, 772.4, 772.5, 772.6, 514/772.7, 781, 901; 424/400, 484, 486, 424/487, 488
See application file for complete search history.

(56) References Cited

U.S. PATENT DOCUMENTS

| | | | |
|---|---|---|---|
| 4,615,697 A | | 10/1986 | Robinson |
| 4,738,842 A | * | 4/1988 | Dow et al. ............... 514/448 |
| 4,851,393 A | * | 7/1989 | Rha et al. ............... 514/54 |
| 5,081,158 A | | 1/1992 | Pomerantz |
| 5,403,578 A | * | 4/1995 | Gordon ............... 424/53 |
| 5,458,879 A | * | 10/1995 | Singh et al. ............... 424/400 |
| 5,462,749 A | | 10/1995 | Rencher |
| 5,474,768 A | | 12/1995 | Robinson |
| 5,543,150 A | | 8/1996 | Bologna et al. |
| 5,667,492 A | | 9/1997 | Bologna et al. |
| 5,900,230 A | | 5/1999 | Cutler |
| 5,968,500 A | | 10/1999 | Robinson |
| 5,989,535 A | * | 11/1999 | Nayak ............... 424/78.02 |
| 6,017,521 A | | 1/2000 | Robinson et al. |
| 6,056,950 A | * | 5/2000 | Saettone et al. ............... 424/78.04 |
| 6,071,959 A | | 6/2000 | Rhodes et al. |
| 6,103,266 A | | 8/2000 | Tapolsky et al. |
| 6,166,044 A | | 12/2000 | Sandborn et al. |
| 6,375,963 B1 | * | 4/2002 | Repka et al. ............... 424/402 |
| 6,632,423 B2 | * | 10/2003 | Jafari et al. ............... 424/78.35 |
| 2002/0076421 A1 | * | 6/2002 | Dobrozsi ............... 424/400 |
| 2002/0103219 A1 | | 8/2002 | Jacob |
| 2002/0142042 A1 | | 10/2002 | Mumper et al. |
| 2003/0098438 A1 | * | 5/2003 | Haslin ............... 252/70 |
| 2005/0281862 A1 | * | 12/2005 | Karakelle et al. ............... 424/427 |

FOREIGN PATENT DOCUMENTS

| | | |
|---|---|---|
| EP | 0765664 A | 4/1997 |
| EP | 0765664 A1 | 4/1997 |
| GB | 1593097 | 7/1981 |
| GB | 1593097 A | 7/1981 |
| NZ | 285761 | 5/1997 |
| NZ | 282537 | 9/1998 |
| US | 6071959 A | 6/2000 |
| US | 6103266 A | 8/2000 |
| US | 6166044 A | 12/2000 |
| WO | 9609829 | 4/1996 |
| WO | 9609829 A | 4/1996 |
| WO | 9801112 | 1/1998 |
| WO | 9801112 A | 1/1998 |
| WO | 9963986 A | 12/1999 |
| WO | 0050078 | 8/2000 |
| WO | 0209637 A2 | 2/2002 |

OTHER PUBLICATIONS

Busche et al, Topical Drug Classification, Intl Hournal of Pharmaceutics, 295 (2005) 101-112.*
DeCordi, D, Martina, S. "Gelclair: potentially an efficacious treat for chemotherapy-induced mucositis", 2001, 10-12.
Innocenti, M. Moscatelli, G, Lopez, S. "Efficacy of Gelclair in Reducing Pain in Patients with Oral Lesions-Preliminary Findings from an Open Pilot Study", 2001.
Berndtson, J. "A Preliminary Study of Orassist (Gelclair) in the management of Oral Mucositis", 2001, 17-21, Svensk Sjukhustandlak artidning.

(Continued)

*Primary Examiner*—Frederick Krass
*Assistant Examiner*—Benjamin Packard
(74) *Attorney, Agent, or Firm*—Antoinette F. Konski, Esq.; Foley & Lardner LLP

(57) ABSTRACT

Stable, viscous, mucoadhesive aqueous compositions which are useful for the prevention and treatment of ulcerative, inflammatory, and/or erosive disorders of mucous membranes, especially mucositis.

16 Claims, 5 Drawing Sheets

OTHER PUBLICATIONS

Editio Cantor Verlag "Rote Liste 2000", 2000, 1-5 7,9,12-16, 18,19,21, Rote Liste Service Aulendorf Xp002203083.

Innocenti, M., Dr. "Clinical Evaluation of Gelcair Concentrated Oral Gel, A New Option for Treating Painful Oral Condition" pp. 1-4, Milan, Italy, 2001.

PDR 21 Edition 2000, Physicians Desk Reference for Nonprescription Drugs and Dietary Supplements, pp. 640 and 787.

Sedano, H., Dr. "Oral Complications During Cancer Treatment" Jun. 13, 2002, pp. 1-5.

Korbar-Smid J. et al. "An Oxtetracycline Formulation to be Applied at the Oral Mucosa" Aug. 5, 1975, pp. 271-276, University of Ljubljana.

Dixon, J. "Search Conducted on Hyaluronic Acid and Mucositis" May 29, 2002, all pages, U.S.

Kaken Seiyaku KK, Abstract, JP 59186913, Apr. 4, 1983.

Tsumura & Co., Abstract JP 8291083, Apr. 17, 1995.

Cheng, K.K.F. et al. "Evaluation of an oral care protocol intervention in the prevention of chemotherapy-induced oral mucositis in paediatric cancer patients" *Eur. J. Cancer*(Nov. 2001) 37(16):2056-63.

Demarosi, F. et al. "Prevention and Treatment of Chemo- and Radiotherapy-Induced Oral Mucosistis" *Minerva Stomatol.* (May, 2002) 51(5):173-186.

Dodd, M.J. et al. "Risk Factors for Chemotherapy-Induced Oral Mucositis: Dental Appliances, Oral Hygiene, Previous Oral Lesions, and History of Smoking" *Cancer Inves.* (1999) 17(4):278-284.

Epstein, J.B. and A.W. Chow "Oral Complications Associated with Immunosuppression and Cancer Therapies" *Infectious Disease Clinics of North America* (Dec. 1999) 13(4):901-923.

Fulton, J.S. et al. "Management of Oral Complications" *Semin. Oncol. Nurs.* (Feb. 2002) 18(1):28-35.

Ghate, J.V. and J.L. Jorizzo "Behçet's Disease and Complex Aphthosis" *J. Am. Acad. Dermatol.* (Jan. 1999) 40(1):1-18.

Miles, D.A. and M.M. Howard "Disorders Affecting the Oral Cavity: Diagnosis and Management of Oral Lichen Planus" *Dermatologic Clinics* (Apr. 1996) 14(2):281-290.

Morales, A. et al. "Treatment of Refractory Interstitial Cystitis" *Int. Urogynecol. J.* (1996) 7(4):215-220.

Plevová, P. "Prevention and treatment of chemotherapy- and radiotherapy-induced oral mucositis: a review" *Oral Oncology* (Sep. 1999) 35:435-470.

Popovsky, J.L. and C. Camisa "New and Emerging Therapies for Diseases of the Oral Cavity" *Dermatologic Clinics* (Jan. 2000) 18(1):113-125.

Sonis, S.T. et al. "Validation of a New Scoring System for the Assessment of Clinical Trial Research of Oral Mucositis Induced by Radiation or Chemotherapy" *Cancer* (May 15, 1999) 85(10):2103-2113.

Sonis, S.T. et al. "Oral Complications of Cancer Therapy" *Oncology* (May 2002) 16(5):680-686, 691-692, 695.

Worthington, H.V. et al. "Interventions for treating oral mucositis for patients with cancer receiving treatment" *Cochrane Database Syst. Rev.* (2002) 1:CD001973, located at http://web19.epnet.com/citation.asp?rds=1&sxp=32&...%5B0+%2Dproximity+op.

International Search Report for PCT/US02/04577 dated Jun. 21, 2002.

Written Opinion for PCT/US02/04577 dated Sep. 16, 2003.

International Preliminary Examination Report for PCT/US02/04577 dated Jan. 12, 2004.

Buhse et al. (2005) "Tropical drug classification," *International Journal of Pharmaceuticals* 295:101-112.

Khandwala et al. (1997) "5% Amlexanox oral paste, a new treatment for recurrent minor aphthous ulcers: I. Clinical demonstration of acceleration of healing and resolution of pain," *Oral Surg Oral Med Oral Pathol Oral Radiol Endod* 83(2):222-230.

\* cited by examiner

LIQUID FORMULATIONS FOR THE PREVENTION AND TREATMENT OF MUCOSAL DISEASES AND DISORDERS

Continuation-in-part of U.S. patent application Ser. No. 10/077,459, filed Feb. 15, 2002, which in turn claims priority under 35 U.S.C. Section 119(e) to U.S. Provisional Application Ser. No. 60/269,049, filed Feb. 15, 2001, now abandoned. The content of each application is hereby incorporated by reference into the present disclosure.

FIELD OF THE INVENTION

The present invention relates to compositions and methods of manufacture of stable, viscous, mucoadhesive liquid and mucoadhesive gel formulations, and the use of these compositions to coat mucocutaneous surfaces, in particular the oral cavity, to prevent and/or treat mucosal diseases and disorders, including those which are ulcerative, inflammatory, and/or erosive, especially mucositis induced by chemotherapy and/or radiation therapy. The liquid dosage forms are sufficiently mobile to coat a wide area of the mucosal surface, but are also mucoadhesive and viscous to provide prolonged retention on the surface of the mucosa. The liquid compositions may be used without a known pharmaceutically active compound. One or more pharmaceutically active compounds may be included in the formulation to provide additional benefit in the topical treatment of diseases and disorders of the mucosa.

BACKGROUND OF THE INVENTION

Mucous membranes provide a protective layer on the surface of several body cavities, such as the oral cavity, the nasal cavity, the gastrointestinal and respiratory tracts, the vagina, and the bladder. Cells within or glands adjacent to these membranes secrete mucus, a fluid or gel primarily composed of water, lipids, inorganic salts and mucin glycoproteins, which serve to form a protective barrier to inhibit passage of harmful materials to the underlying tissue. There are several diseases and disorders of these mucosal surfaces which can result in severe pain, irritation, erythema, and/or ulceration. Examples of such diseases in the oral cavity include aphthous ulcers, bullous pemphigoid, oral lichen planus, and oral mucous membrane contact dermatitis. Many other ulcerative mucocutaneous diseases are known. There are also painful ulcerative disorders of mucosal surfaces which result as an adverse side-effect in certain therapies, such as chemotherapy and radiation therapy. Mucositis is an adverse side-effect which impacts the oral cavity in patients undergoing therapy for a number of conditions including cancer, AIDS, and in bone marrow transplantation therapy.

Overview of Oral Mucositis

Oral mucositis is a significant problem in patients receiving chemotherapy or radiation therapy. Estimates of oral mucositis in cancer therapy range from 40% of those receiving standard chemotherapy to 76% of bone marrow transplant patients. Virtually all patients who receive radiation therapy to the head and neck area develop oral complications. Mucositis is not only painful, but it also can limit adequate nutritional intake and decrease the willingness of patients to continue treatment. More severe mucositis with extensive ulceration may require costly hospitalizations with parenteral nutrition and narcotics. Mucositis diminishes the quality of life and may result in serious clinical complications. A healthy oral mucosa serves to clear microorganisms and provides a chemical barrier that limits penetration of many compounds into the epithelium. A mucosal surface that is damaged increases the risk of a secondary infection and may even prove to be a nidus for systemic infection. Mucositis may result in the need to reduce dosage in subsequent chemotherapy cycles or to delay radiation therapy, which may ultimately affect patient response to therapy.

Normally, cells of the mouth undergo rapid renewal over a 7- to 14-day cycle. Both chemotherapy and radiation therapy interfere with cellular mitosis and reduce the ability of the oral mucosa to regenerate. Cancer chemotherapeutic drugs that produce direct stomatotoxicity include the alkylating agents, antimetabolites, natural products, and other synthetic agents such as hydroxyurea and procarbazine hydrochloride. Typical sequelae of these cytotoxic agents include epithelial hyperplasia, collagen and glandular degeneration, and epithelial dysplasia. Mucositis is an inevitable side effect of radiation. The severity of the mucositis is dependent on the type of ionizing radiation, the volume of irradiated tissue, the dose per day, and the cumulative dose. As the mucositis becomes more severe, pseudo membranes and ulcerations develop. Poor nutritional status further interferes with mucosal regeneration by decreasing cellular migration and renewal.

Direct stomatotoxicity is usually seen 5 to 7 days after the administration of chemotherapy or radiation therapy. In the nonmyelosuppressed patient, oral lesions heal within 2 to 3 weeks. The no keratinized mucosa is most affected. The most common sites include the labial, buccal, and soft palate mucosa, as well as the floor of the mouth and the ventral surface of the tongue. Clinically, mucositis presents with multiple complex symptoms. It begins with asymptomatic redness and erythema and progresses through solitary white elevated desquamative patches that are slightly painful to contact pressure. Following these large, acutely painful contiguous pseudo membranous lesions will develop with associated dysphagia and decreased oral intake. Histopathologically, edema of the retepegs is noted, along with vascular changes that demonstrate a thickening of the tunica intima with concomitant reduction in the size of the lumen and destruction of the elastic and muscle fibers of the vessel walls. The loss of the epithelial cells to the basement membrane exposes the underlying connective tissue stroma with its associated innervation, which, as the mucosal lesions enlarge, contributes to increasing pain. Oral infections, which may be due to bacteria, viruses, or fungal organisms, can further exacerbate the mucositis as well as lead to systemic infections. If the patient develops both severe mucositis and thrombocytopenia, oral bleeding may occur that is very difficult to treat.

A mucositis grading system gives the physician the ability to assess the severity of the mucositis in terms of both the pain and the patient's ability to maintain adequate nutrition so that a treatment plan can be appropriately constructed. There are many different grading systems; most are based on two or more clinical parameters, including erythema, pain, and problems with eating. An example of a common grading system is that proposed by the National Cancer Institute, which uses a numbering scale of 0 to 4. Grade 0 means no mucositis; grade 1, the patient has painless ulcers, erythema, or mild soreness; grade 2, the patient has painful erythema, edema, or ulcers but can eat; grade 3, the patient has painful erythema, edema, or ulcers and cannot eat; and grade 4, the patient requires parenteral or enteral support.

(source: DeVita: Cancer: Principles and Practice of Oncology, 5th ed., Copyright© 1997 Lippincott-Raven Publishers)

Current Methods for the Prevention and Treatment for Mucositis

In spite of the significance of the problem, there are currently no well-established procedures and formulations for the prevention and treatment of mucositis. As a result, there is no standardized approach, and many institutes have adopted treatment regimens based on little or no supporting data of safety and efficacy. There is even disagreement on whether good oral hygiene is beneficial (for example: Dodd M J, Miaskowski C, Shiba G H, Dibble S L, Greenspan D, MacPhail L, Paul S M, Larson P, Risk factors for chemotherapy-induced oral mucositis: dental appliances, oral hygiene, previous oral lesions, and history of smoking, Cancer Invest 1999;17(4):278–84 and Cheng K K, Molassiotis A, Chang A M, Wai W C, Cheung S S. Evaluation of an oral care protocol intervention in the prevention of chemotherapy-induced oral mucositis in pediatric cancer patients, Eur J Cancer 2001 November;37(16):2056–6). Good oral hygiene is typically recommended, supplemented by formulations which are compounded locally and primarily used to provide prophylaxis. Thus, patients will be asked to use ice, saline rinses, bicarbonate rinses, or rinse with antimicrobial formulations such as acyclovir or chlorhexidine. (Fulton J S, Middleton G J, McPhail J T, Management of oral complications, Semin Oncol Nurs 2002 February;18(1):28–35). Regimens commonly used for the treatment of mucositis and its associated pain include a local anesthetic such as lidocaine or Dyclone, Maalox or Mylanta, diphenhydramine (Benadryl), nystatin, or sucralfate. These agents are either used alone or in different combinations of the above medications made into a mouthwash. Other agents used less commonly include Kaopectate, allopurinol, vitamin E, beta-carotene, Kamillosan liquid, aspirin, antiprostaglandins, prostaglandins, silver nitrate, and antibiotics. Oral and sometimes parenteral narcotics are used for pain relief. (DeVita: Cancer: Principles and Practice of Oncology, 5th ed., Copyright© 1997 Lippincott-Raven Publishers). Recent reviews of current treatment options and of investigational clinical trials indicated that most agents and options failed to show any benefit in the prevention and/or treatment of mucositis. (Worthington H V, Clarkson J E, Eden O B, Interventions for treating oral mucositis for patients with cancer receiving treatment, Cochrane Database Syst Rev 2002;(1): CD001973; Demarosi F, Bez C, Carrassi A., Prevention and treatment of chemo- and radiotherapy-induced oral mucositis. Minerva Stomatol 2002 May;51(5):173–86).

A recent review (Sonis S T, Fey E G, Oral Complications of Cancer Therapy, Oncology 2002, 16:680–695) provides an overview of the many agents which have been evaluated in clinical studies for the prevention and treatment of mucositis, and concludes "there is no effective approved treatment for mucositis", and that there is no conclusive evidence that experimental agents which are currently the subjects of clinical studies will provide benefit to future patients. While ongoing studies are providing a better understanding of the etiology of mucositis, it may be some time before this knowledge can be translated into effective new treatments. In the meantime, the main approaches are based upon theory, and it is anticipated that it may be many years before rationale drug design can be applied based upon a better understanding of etiology.

The current approaches can be classified as "palliative, cytoprotective, anti-inflammatory, and antimicrobial agents, and cytokines" (Plevova P: Prevention and treatment of chemotherapy- and radiotherapy-induced oral mucositis: A review. Oral Oncol 35:453–470, 1999; Sonis S T, Fey E G, Oral Complications of Cancer Therapy, Oncology 2002, 16:680–695).

Examples of each type are:
i) Palliative: saline and bicarbonate rinses, sucralfate suspensions, and topical analgesics (for example, viscous lidocaine, dyclonine, diphenhydramine, and loperamide.
ii) Cytoprotective: Ice chips, allopurinol, glutamine, pentoxifylline, Ethyol, and antioxidants such as vitamins C and E.
iii) Anti-inflammatories: Benzydamine, indomethacin, and amlexanox.
iv) Anti-microbials: chlorhexidine, povidone iodine, the protegrin IB-367.
v) Cytokines: Keratinocyte growth factor, transforming growth factor-beta 3, and interleukin-11, and the colony-stimulating factors: G-CSF and GM-CSF.

Topical coating agents such as magnesium hydroxide (e.g., Milk of Magnesia), Kaopectate (Pharmacia & Upjohn, Columbus, Ohio), OraRinse (Carrington Laboratories), GelClair (Sinclair Pharmaceuticals) and aluminum hydroxide gel (Amphojel; Wyeth-Ayerst, Philadelphia, Pa.) may provide some symptomatic relief of the lesions associated with mucositis (J B Epstein, A W Chow, Oral complications associated with immunosuppression and cancer therapies, Infectious Disease Clinics of North America, 1999, 13(4), 901–923).

While palliation provides temporary relief, none of the above treatments provides any proven benefit in preventing or treating mucocitis, with the possible exception of the use of ice chips during 5-FU therapy. Therefore, the development of a product which provides clinically proven benefit for the prevention and/or treatment of mucositis remain a major unmet medical need.

SUMMARY OF THE INVENTION

It is an aim of the present invention to provide viscous, mucoadhesive liquid and mucoadhesive gel formulations to be used for the prevention and treatment of mucocutaneous disorders. The formulation may be used with or without one or more active pharmaceutical agents. These formulations are especially beneficial in diseases and conditions in which a wide area of the mucosal surface requires treatment, but the formulations may also be used in treating small areas of the mucosal surface.

In order that mucocutaneous disorders are treated effectively, it is preferred that the lesion is in contact with the liquid or gel, mucoadhesive formulation for the period of time required to derive benefit. To grant such benefit, this invention describes mucoadhesive, viscous liquid and mucoadhesive gel formulations which may or may not contain one or more pharmaceutically active ingredients. The liquid can readily be applied to the affected region of the mucosa by methods known in the art, while the high viscosity and mucoadhesion will cause liquid or gel to remain in contact with the lesion for extended periods. The formulations of the present invention may be applied to treat mucocutaneous lesions in a variety of body compartments, including, but not limited to, the oral cavity, the nasal cavity, the esophagus, the rectum, the bladder, and the vagina.

The present invention involves a composition for the treatment and prevention of mucocutaneous disorders. This composition of the present invention, in one embodiment, comprises an amount of a mucoadhesive effective to coat the mucocutaneous area being treated and also a therapeutically or prophylactically active drug for a mucocutaneous disorder.

In an important embodiment, the mucoadhesive is at a viscosity-inducing concentration. In another embodiment of the present invention, the mucosal drug delivery composition useable in the treatment or prevention of a mucocutaneous disorder is described. This composition comprises an amount of a mucoadhesive to form an effective coat in the mucocutaneous area being treated, a viscosity-inducing agent and a therapeutic or prophylactic drug for mucocutaneous disorders. The mucoadhesive of the present invention in one embodiment may be a natural or synthetic linear or cross linked polymer. This mucoadhesive can be for example a linear or cross-linked polyacrylic acid, carboxymethylcellulose, hydroxyalkylcellulose, polyvinylpyrrolidone dextran sulfate, dermatan sulfate, a water-soluble vinyl polymer, guar gum, xanthan gum tragacanth gum and pectin or chitosan. In the composition of the present invention a mucoadhesive is generally at a concentration between about 0.1 w/w % and about 3.0 w/w %. In preferred embodiments, the mucoadhesive of the present invention will contain cross-linked polyacrylic acid hydrogels plus optional linear polyacrylate and/or polymethacrylate and/or linear copolymers derived from acrylate and methacrylate monomers. Useable viscosity-inducing agents are many and include agar, bentonite, glycerin, providone, kaolin, tragacanth, sodium alginate and cross-linked polyacrylic acids. The composition of the present invention is preferably at a pH between about 6.5 and about 9.5.

Among the mucocutaneous disorders treatable by their methods and compositions of the present invention are: mucositis, Bechet's disease, apthous ulcer, bullous pemphigoid, chemical cystitis, radiation cystitis, erythema multiforme, esophagitis, interstitial cystitis, oral Lichen planus, pemphigus, radiation proctitis, or ulcerative colitis.

An important aspect to the present invention involves a method for the prevention or treatment of mucocutaneous disorders. This method involves identifying a patient having or possibly developing a mucocutaneous disorder. Next in this method is the administration to the patient of a formulation comprising a mucoadhesive agent in an amount effective to prevent or treat the mucocutaneous disorder. Of course, this formulation may and often does include a viscosity-inducing agent and/or a viscosity-enhancing concentration of mucoadhesive. Mucocutaneous disorders treatable by this method are described above. The liquid formulation of this invention are often more useful when possessing pseudoplastic behavior, which provides for reduced viscosity during application, allowing the liquid to cover the mucosa more readily, and for increased viscosity of the liquid when in place on a mucocutaneous area. In terms of the length of treatment, this will vary according to the severity and type of disorder. It is expected that the alleviation of mucocutaneous disorders should be visible to anyone treating the patient and that the method of treatment should continue until recovery is clear. This may take from hours to days to weeks, depending upon the situation. Preferred mucoadhesive agents for this method are described above. Likewise, for viscosity-inducing agents.

DETAILED DESCRIPTION OF THE PREFERRED EMBODIMENTS

Figure 1:
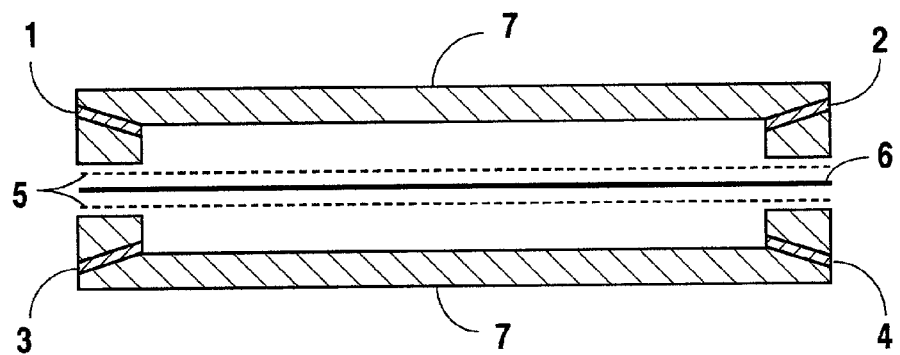
FIGS. 1 and 1a show an in vitro model developed to demonstrate the enhanced delivery of active pharmaceutical ingredients to the surface of mucosal membrances.
Figure 1A:
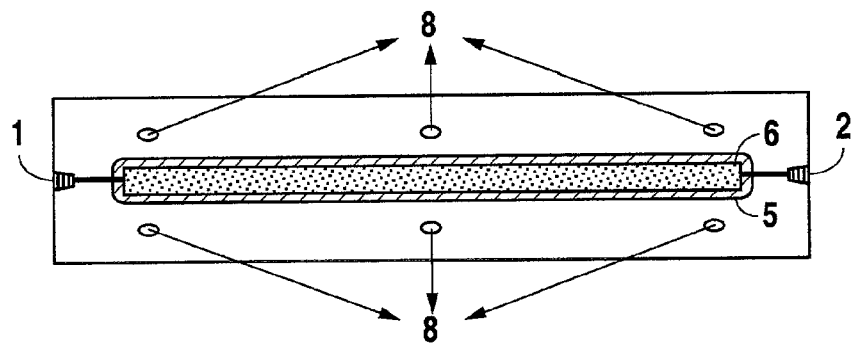

The present invention describes formulations for the prevention and treatment of disorders of mucous membranes in humans and animals. The liquid or gel formulations of the present invention are ideally suited to treat diseases and disorders which affect a wide area of the mucosal surface, but they also provide the opportunity to treat discrete, localized lesions, especially in the oral cavity. The mucous membranes which may be treated by the compositions described in this patent include, but are not limited to, those in the oral cavity, the nasal cavity, the gastrointestinal and respiratory tracts, the vagina, and the bladder. Inflammatory, erosive, and/or ulcerative diseases which can be treated by topical application of the compositions described in this patent include, but are not limited to, aphthous ulcers, Behget syndrome, bullous pemphigoid, chemical or radiation-induced cystitis, erythema multiforme, esophagitis, interstitial cystitis, mucositis, oral lichen planus, pemphigus, and radiation proctitis. In conditions such as aphthous ulcers, chemical or radiation-induced cystitis, mucositis, and radiation proctitis, when the onset of the inflammatory, erosive, and/or ulcerative condition may be forecast (for example, by prodromal sensations in the case of aphthous ulcers, and by initiation of chemotherapy and/or radiation therapy in the treatment of cancer), the compositions of this invention might be applied prior to the formation of lesions, or at the commencement of therapy to prevent or delay the onset of inflammatory, erosive, and/or ulcerative lesions. While a mucoprotective agent may be a mucoadhesive alone, a viscous mucoadhesive liquid or mucoadhesive gel arepreferred particularly when a pharmaceutical agent is present to be selectively transmitted to a mucosal target.

As described later in the Examples section, one of the viscous, mucoadhesive formulations of the current invention, a viscous liquid which is composed entirely of pharmaceutically-accepted excipients, demonstrated a surprising result in a clinical study. This study examined the degree of mucositis in patients receiving radiotherapy for head and neck cancer. The mean and median mucositis scores for patients rinsing six times a day with one of the viscous, mucoadhesive solutions of the current invention for the duration of radiation therapy (6–7 weeks), with or without concombinant chemotherapy, were much lower than the scores for patients who did not use this rinse.

Furthermore, mucoadhesive liquid/gel formulations of the current invention which are also composed entirely of pharmaceutically-accepted excipients, demonstrated a surprising results in a hamster model of radiation induced mucositis.

There is currently no complete explanation of why the viscous, mucoadhesive liquids and gels of the current invention without a known active pharmaceutical ingredient should provide such benefit to patients. The following are considered viable possibilities, but this invention should not be considered as limited to any one of these possibilities:

A viscous, mucoadhesive solutions provides a layer on the surface of the mucosa for an extended period, and this may have a beneficial effect, for example, a moisturizing or barrier effect, so limiting the damage to the mucosal surface caused by disease, or injury from ionizing radiation and/or chemotherapeutic agents. Thus, it is envisioned that any aqueous formulation which is formulated with non-toxic and non-irritating excipients and providing a liquid or gel-which is both viscous and mucoadhesive might be expected to provide benefit to patients suffering a disease or disorder of the mucosa.

It is known that polyanionic carbohydrate polymers and oligomers can have a beneficial effect in the treatment of mucosal disorders. For example, pentosan polysulfate and hyaluronic acid are known to provide benefit to patients with interstital cystitis (Morales A, et al, Treatment of refractory interstitial cystitis, Int Urogynecol J Pelvic Floor Dysfunct 1996;7(4):215–20). It is quite possible that other polyanionic and polycationic compounds, whether carbohydrate, of natural origin or synthetic, may also provide benefit in the prevention and treatment of mucosal disorders. Linear and partially cross-linked polyanionic polymers are included in the formulation used in the product demonstrating benefit in the mucositis clinical study described in the examples.

Other components of the formulation used in the clinical study, benzyl alcohol, citric acid, glycerin, polysorbate 60, and saccharin, alone or in combination with each other and/or the other excipients of the formulation may have a beneficial effect. Other preservatives, humectants, emulsifying agents, antioxidants, antimicrobial agents, solubilizing agents, and other excipients known in the art in the formulation of liquid pharmaceutical products, alone or in combination, may also provide for, or enhance, the beneficial properties on mucosal surfaces, when formulated to provide a viscous, mucoadhesive solution.

Other components of the liquid/gel formulations used in the hamster model of mucositis (phenoxyethanol, glycine, glycerol, ethanol) alone or in combination with each other and/or the other excipients of the formulation may have a beneficial effect. Other preservatives, humectants, emulsifying agents, antioxidants, antimicrobial agents, solubilizing agents, and other excipients known in the art in the formulation of gel pharmaceutical products, alone or in combination, may also provide for, or enhance, the beneficial properties on mucosal surfaces, when formulated to provide a mucoadhesive gel.

Viscous, mucoadhesive formulations for the prevention and treatment of mucosal diseases and disorders may additionally be formulated with one or more compounds known to be pharmaceutically active. Addition of further pharmaceutically active compounds could provide greater benefit to patients in the prevention and treatment of mucosal disorders. Examples of pharmaceutically active compounds which could be incorporated in the viscous, mucoadhesive solutions of this invention as provided later in this section.

Aqueous solutions of pharmaceutically-active compounds are well known in the art as convenient drug delivery formulations. Such formulations are most useful for oral delivery, when the solution is swallowed, and the drug is presented to the stomach and gastrointestinal tract in a form which is amenable to rapid absorption. Aqueous solutions are also used to deliver drugs to mucosal tissue. In general, aqueous solutions used to deliver pharmaceuticals tend to be non-viscous and non-mucoadhesive. For oral delivery, this property is undesirable, as it minimizes the amount of drug which is retained in the oral cavity and esophagus, while maximizing that delivered to the stomach and gastrointestinal tract. One preferred drug for the treatment of mucocutaneous disorders is amlexanox.

For topical treatment of mucosal membranes, aqueous solutions of pharmaceutically-active compounds offer the advantage over other dosage forms in that a wide area of the mucosa can be readily covered with the solution, which is of benefit if the area to be treated is not a single, discrete region. Also, mucosa not readily accessible can be treated using aqueous solutions of pharmaceutically-active compounds and simple methods of application. However, formulations which are non-mucoadhesive and non-viscous are less than ideal for delivery of drugs to mucosal surfaces. Such solutions will be rapidly removed from the area being treated, for example, because the liquid flows from the site of application under the influence of gravity, and/or because the natural secretions of mucosal membranes carry the solution from the site of application.

The present invention involves a finding that neither high viscosity nor mucoadhesion alone confers ideal properties. A viscous but non-mucoadhesive liquid will not be held in place on the mucosal surface. Instead, a non-mucoadhesive solution will readily be lost from the point of application, for example, under the influence of gravity, and/or through natural movements of the membrane and surrounding structures, and/or the flow of natural secretions. In an aqueous liquid formulation which is mucoadhesive but has low viscosity, only a thin layer of the liquid which is adjacent to the mucosa may be held in place, but the bulk of the liquid might rapidly flow from the site of application under the influence of gravity and/or be readily removed by the natural secretions of mucosal membranes. In a mucoadhesive, viscous liquid formulation, the liquid will adhere to the mucosa, while the high viscosity of the liquid will reduce the rate of removal of the bulk of the liquid from the site of application. In some cases a low viscosity mucoadhesive may provide effective treatment, especially when pharmaceutical agents are not required. A mucoadhesive agent may itself be a viscosity-inducer and thus serve two purposes. The term "viscosity-inducing" is meant to mean enhancement of the aqueous mucoadhesive layer that adheres to mucosal areas.

For most liquids, viscosity remains constant over a wide range of shear rates. This phenomenon is known as Newtonian viscosity, and liquids which display this property are called Newtonian liquids. Liquids in which viscosity varies with shear rate are termed non-Newtonian. There are several known non-Newtonian profiles. One of these profiles is termed pseudoplastic, and liquids which fall into this category demonstrate a decrease in viscosity as shear rate increases. Preferred formulations of the current invention are pseudoplastic, and demonstrate a decrease in viscosity at low shear rates. Pseudoplasticity benefits the application of the formulations of the current invention by virtue of the fact that application of shear (for example, swishing the liquid in the mouth) reduces the viscosity, so allowing the liquid to flow and coat the mucoscal surface more readily. Once the shear forces are discontinued, the viscosity of the liquid increases, as required (in combination with mucoadhesion) for prolonged attachment to the mucosal surface.

Formulations of the current invention are viscous, free-flowing liquids or mobile gels that are either Newtonian or pseudoplastic. The ability to flow freely or be spread freely is advantageous in order to readily coat either a selected region or a wide area of the affected mucosal membrane, and to coat mucosal membranes not readily accessible to simple application. The solutions of the current invention will have viscosities at zero shear in the range 100–20,000 cP.

The stable, viscous, mucoadhesive liquid formulations of the present invention may be applied to mucosal membranes for the delivery of pharmaceutically active compounds to the mucosal membranes for prevention and/or treatment of disorders or diseases of these membranes. The liquid may be applied, e.g., to the following mucosal surfaces; the oral cavity, the nasal cavity, the gastrointestinal and respiratory tracts, the vagina, and/or the bladder. The formulations of the current invention may also be applied to other mucous membranes for the prevention and treatment of disorders and diseases. Many methods known in the art for the delivery of liquids to body compartments may be used.

For treatment of disorders and diseases of the oral cavity, the stable, viscous, mucoadhesive liquid formulations of the current invention may be taken by mouth and distributed throughout the oral cavity by a swishing action, or by the patient adopting a slow circulating movement of the head. Excess solution can either be swallowed or expelled. For treatment of disorders and diseases of the oral cavity, the stable, mucoadhesive gel formulations of the current invention may be taken by mouth and distributed throughout the oral cavity by the action of the tongue and/or use of a swab or similar device. Excess gel can either be swallowed or expelled.

For treatment of disorders and diseases of the esophagus, the stable mucoadhesive liquid and gel formulations of the current invention can be swallowed with minimal contact of the oral cavity, or administered by gavage, or by spraying the liquid into the throat.

For treatment of disorders and diseases of the nasal cavity, the stable mucoadhesive liquid and gel formulations of the current invention can be delivered as droplets or by spraying the liquid into the nose.

For treatment of disorders and diseases of the bladder, the stable, mucoadhesive liquid or gel formulations of the current invention can be delivered by intravesical administration.

For treatment of disorders and diseases of the rectum and lower gastrointestinal tract, the stable mucoadhesive liquid or gel formulations of the current invention can be administered by catheter or enema.

Other methods to apply the stable, viscous, mucoadhesive liquid formulations and stable mucoadhesive gel formulations of the current invention to mucosal tissues are known to those skilled in the art.

Pharmaceutically active compounds which may be formulated with the stable mucoadhesive liquid and gel formulations of the current invention for topical treatment of a mucosa can include, either alone or in combination, one or more of the following classes of drugs: anti-allergy compounds, anti-inflammatory analgesic agents, steroidal and non-steroidal anti-inflammatory agents, antioxidant compounds, analgesics, antihistamines, local anesthetics, bactericides and disinfectants, vasoconstrictors, hemostatics, antibiotics, keratolytics, cauterizing agents, antiviral drugs, growth factors, supplements and other potential agents for treatment of mucositis. Other classes of pharmaceutically active agents may also be formulated with the stable mucoadhesive liquid and gel formulations of the current invention.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc.

Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, etc.

Examples of antioxidant compounds include ascorbic acid, dehydroascorbic acid, alpha-tocopherol, glutathione, beta-carotene, azelastine, N-acetyl-L-cysteine, allopurinol, flavanoids, etc.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc.

Examples of local anesthetics include dibucaine hydrochloride, dibucaine, lidocaine hydrochloride, lidocaine, benzocaine, p-buthylaminobenzoic acid 2-(di-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include phenoxyethanol. triclosan, thimerosal, phenol, thymol, benzalkonium chloride, benzethonium chloride, chlorhexidine, povidone iodide, cetylpyridinium chloride, eugenol, trimethylammonium bromide, etc.

Examples of vasoconstrictors include naphazoline nitrate, tetrahydrazoline hydrochloride, oxymetazoline hydrochloride, phenylephrine hydrochloride, tramazoline hydrochloride, etc.

Examples of hemostatics include thrombin, phytonadione, protamine sulfate, aminocaproic acid, tranexamic acid, carbazochrome, carbaxochrome sodium sulfanate, rutin, hesperidin, etc.

Examples of antibiotics include penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, cycloserine, and clindamycin.

Examples of keratolytics include salicylic acid, podophyllum resin, podolifox, and cantharidin. Examples of cauterizing agents include the chloroacetic acids and silver nitrate.

Examples of antiviral drugs include protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of anti-allergy compounds include alopatadine, astemizole, cromolyn, fenpiprane, repirinast, tranilast, traxanox, etc.

Examples of growth factors, supplements and other potential agents for treatment of mucositis includes keratinocyte growth factor, granulocyte-colony-stimulating factor, transforming growth factor-beta3, sucralfate, L-glutamine, aminoacids, lisofylline, IL-15, antimicrobial peptides and histamine.

The amount of pharmaceutically active compound(s) to be used depends on the desired treatment strength, although preferably, the pharmaceutical component comprises 0.001 to 30% by weight of the formulation, and more preferably between 0.005 and 20% by weight.

In addition to the preferred requirements of mucoadhesion and viscosity as described above, it is important, for use of the formulation for the prevention and treatment of mucosal diseases and disorders that the liquid or gel be stable, such that it can be stored at ambient temperatures for many months or years, even when subjected to brief periods of elevated or depressed temperatures, without physical or chemical degradation of the formulation. It is usually desirable to formulate the product without use of any organic solvents, the presence of which might irritate the mucosal lesions being treated, although liquid and gel formulations containing pharmaceutically-acceptable organic solvents are within the scope of this invention provided that the incorporation of such solvents does no harm to the mucosa, and possibly provides benefit; for example, as disinfectants, or to aid the solvation of the mucous membrane to provide more rapid mucoadhesion, or for concentration of the excipients (through evaporation of the solvent following application to the mucosa) to enhance mucoadhesion and/or viscosity following application. Furthermore, it is desirable to formulate the viscous, mucoadhesive solution using only excipients which are accepted by all major pharmaceutical regulating authorities as safe.

The following list provides examples of components of the stable, viscous, mucoadhesive formulations of the current invention:

A linear or cross-linked polymer polyanionic or polycationic polymer which may or may not already be known to provide mucoadhesion. Such polymers include (but are not limited to) linear polyacrylic acid, a cross-linked homopolymer based on acrylic acid, a crosslinked copolymer based on acrylic acid, linear methacrylic acid homopolymers and copolymers, carboxymethylcellulose, hydroxyalkylcellulose, dextran sulfate, dermatan sulfate, and hyaluronic acid. Other mucoadhesive polymers are well-known to those skilled in the art. The mucoadhesive formulations of the current invention can contain a single mucoadhesive component, or mixtures thereof. The preferred mucoadhesive polymers are cross-linked homopolymers and copolymers based on acrylic acid and methacrylic acid, especially the Carbopol and polycarbophil polymers supplied by B.F. Goodrich, and Eudragit polymers supplied by Rohm-Haas; most preferred are Carbopol™, (polymer of acrylic acid cross-linked with polyalkenyl ethers or divinyl glycol) Noveon AA1®, (also called polycarbophil, a salt of polyacrylic acid cross-linked with polyether or divinyl glycol) and Eudragit L-100 (methacrylic acid-ethyl acrylate copolymer (1:1)).

Viscosity enhancement is provided by one or more of the above mentioned mucoadhesive polymers alone or in combination with agar, bentonite, glycerin, povidone, kaolin, and/or tragacanth and sodium alginate. Most preferred is Carbopol in combination with glycerin.

The pH of the solution is adjusted to the final desired pH with any pharmaceutically accepted acid or base. Most preferred is sodium or potassium hydroxide, phosphoric acid, or citric acid. A final pH of 6.5 to 9.5 is preferred.

To prevent microbial growth in the formulation during storage, it is desirable to include a preservative. Preservatives known in the art include benzyl alcohol, benzoate salts, phenoxyethanol, methylparaben, and propylparaben. Phenoxyethanol and benzyl alcohol are the most preferred preservatives.

A humectant is desirable to provide a pleasant mouth-feel in oral applications. Humectants known in the art include cholesterol, fatty acids, glycerin, lauric Acid, magnesium stearate, pentaerythritol, and propylene glycol. Glycerin is preferred.

An emulsifying agent might be necessary, for example to ensure complete dissolution of all excipients, especially hydrophobic components such as benzyl alcohol. Many emulsifiers are known in the art. The preferred emulsifier is polysorbate 60

For oral applications, it may be desirable to add a pharmaceutically acceptable flavoring agent, coloring agent and/or sweetener. Compounds such as saccharin, glycerin, simple syrup, and sorbitol are useful among those as sweeteners. Saccharin is preferred.

It may be desirable to include other ingredients; for example a pharmaceutically acceptable organic solvent, a buffering agent, an antioxidant, a free radical scavenger, an antimicrobial agent, and/or a coloring agent. The exact formulation of the above ingredients, and the method of manufacture, will be apparent to those skilled in the art. A number of texts provide assistance in the design and manufacture of pharmaceutical formulations, including Remington's Pharmaceutical Sciences, Mack Publishing Company Co., Easton, Pa., and Pharmaceutical dosage forms and drug delivery, Ansel et al, 1995, Williams and Wilkins, Malvern, Pa.

The following examples are provided to demonstrate the beneficial effects of stable mucoadhesive liquids and gels of this invention. Example 4 is provided to demonstrate that both mucoadhesion and viscosity are desired to provide the coating of a liquid on an artificial mucosal surface with extended retention properties. In this in-vitro model of the mucosal surface, a steady flow of artificial saliva across the 'mucosal' surface attempts to remove the liquid coating. The hydrophobic drug amlexanox is used as a marker of film erosion and retention (the latter by delivery of the marker across the model mucous membrane). The study clearly demonstrates that the liquid requires both mucoadhesion and viscosity for retention.

Example 6 presents an analysis of a clinical study of a stable, viscous, mucoadhesive rinse formulation of this invention compared with standard care in patients receiving radiation therapy to the head and neck. This analysis provided the surprising result that the stable, viscous, mucoadhesive rinse formulation of this invention, without an accepted pharmaceutically active ingredient, lowered the mean and median mucositis scores of these patients when compared to a similar group of patients receiving standard care for mucositis.

Example 8 presents the results of a study in Syrian hamsters in which mucositis is induced by irradiation of the oral cavity. Six gel formulations were tested in this model, and the severity of mucositis for each treatment group is expressed as the mean number of days that the animals in each group experienced a mucositis score of three or more. A score of three represents the onset of ulceration, and a higher score represents greater severity of mucositis. The formulations tested in this study are listed in example 7. None of the formulations contain an accepted pharmaceutically-active ingredient. The results of this study clearly demonstrate the following:

a. The most effective formulation (A and B) contains a mixture of two mucoadhesive polymers; Carbopol 971 and Noveon AA1.

b. Across the series, there is a trend that effectiveness generally increases with viscosity, providing evidence of the importance of viscosity of liquid and gel formulations used to treat mucositis.

c. Formulation B (which is the same as A, except that Eudragit L-100 is eliminated) has similar, but slightly reduced efficacy as compared to A; the small difference observed is not statistically significant, and could be explained by viscosity.

d. Formulation C results from elimination of phenoxyethanol from formulation B. Phenoxyethanol is a preservative with known antiseptic and bactericide properties. While formulation C is clearly effective in reducing the severity of mucositis, the formulation is clearly more effective when the antiseptic/bactericide is present.

e. Formulation D is the same as B, except that glycine buffer is replaced by borate buffer. The viscosity of formulation D is marginally lower than that of B, which may account for some of the difference, but the data also indicates that there is a benefit provided by the aminoacid.

f. Formulation E is the same as B, except that Noveon AA1 is eliminated. Viscosity and mucoadhesion are provided only by Carbopol 971. The total concentration of cross-linked acrylate has to be increased to provide a similar viscosity. The poor efficacy of this formulation may be largely due to its reduced viscosity.

g. Formulation F is the same as B except that all of the mucoadhesive polymers are replaced by non-mucoadhesive polymeric thickening agents. The viscosity of this formulation is slightly higher than B, yet it has no efficacy (as compared with saline), demonstrating the importance of mucoadhesion as well as viscosity to efficacy.

EXAMPLES

Example 1

Preparation of Viscous, Mucoadhesive Aqueous Composition

A viscous, mucoadhesive aqueous solution was formulated by adding Carbopol® 971P NF to water using an appropriate mixing apparatus (Master Servodyne® mixer with high-lift blade rotating at 200–300 rpm) to give a clear solution. An aqueous solution of potassium hydroxide was added with stirring to give a clear gel. An aqueous solution of potassium hydroxide, citric acid, saccharin sodium, phosphoric acid and glycerin was added with stirring to give a clear solution. A solution of benzyl alcohol and polysorbate 60 was added with stirring to give a clear solution. The pH was adjusted to 7.0–7.8 with an aqueous solution of phosphoric acid. The resulting product was mixed further for 30 minutes.

The formulation of the product is set out in Table 1:

TABLE 1

| Ingredients | Weight Percent |
| --- | --- |
| purified water | 90.68 |
| 10% potassium hydroxide | c.a. 4.6 |
| benzyl alcohol | 1.50 |
| polysorbate 60 | 0.05 |
| Carbopol ® 971P | 0.35 |
| 0.5% phosphoric acid | c.a. 5.7 |
| citric acid | 0.05 |
| saccharin sodium | 0.40 |
| glycerin | 5.00 |
| Natural orange flavor | 0.05 |

Example 2

Preparation of Viscous, Mucoadhesive Aqueous Composition Containing Amlexanox

The method set out in example one was followed to provide a viscous, mucoadhesive aqueous composition of the following formula:

TABLE 2

| Ingredients | Weight Percent |
| --- | --- |
| purified water | 91.21 |
| potassium hydroxide | 0.60 |
| benzyl alcohol | 1.50 |
| polysorbate 60 | 0.05 |
| Carbopol ® 971P | 0.35 |
| phosphoric acid | 0.13 |
| citric acid | 0.05 |
| saccharin sodium | 0.40 |
| amlexanox | 0.50 |
| glycerin | 5.20 |

Example 3

High Performance Liquid Chromatographic Assay for the Amlexanox

The following HPLC parameters were employed in performing an assaying for amlexanox:

Phenomenex, Prodigy, 5 μm ODS (2), 150 mm×4.6 mm

Mobile Phase: 25% THF/75% 10 mM phosphate buffer, pH 8.0 h. Flow Rate: 1.0 mL/min

Injection Volume: 10 μL i. Detector: UV@ 244 nm

Example 4

Figure 2:
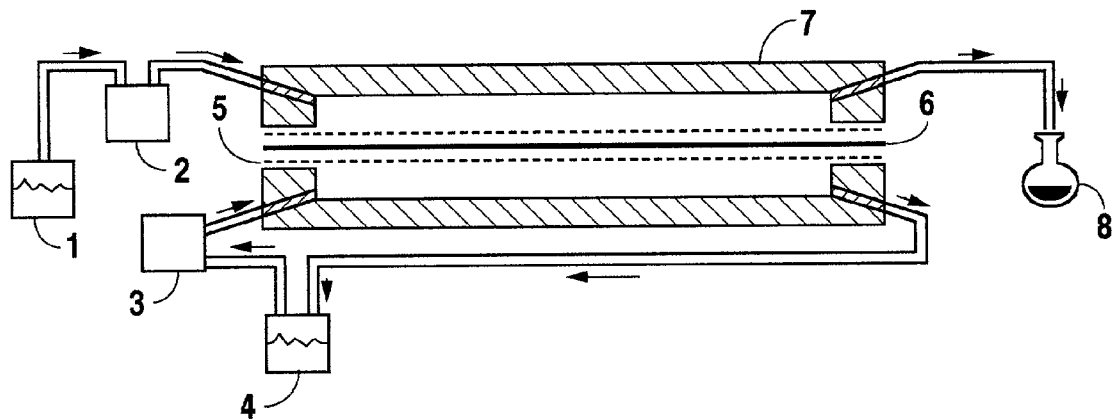
FIG. 2 shows the device described in FIG. 1 is attached to LC pumps 2–3 using 10/31" ferules and large diameter HPLC tubing.

Demonstration of Drug Delivery From Liquid Formulations in an in vitro Model of a Mucosal Surface Referring to FIG. 2, the device described in FIG. 1 is attached to LC pumps 2–3 using 10/32" ferules and large diameter HPLC tubing. One half of the polycarbonate block 7 has a reservoir 1 that provides a continuous flow of artificial saliva across the Spectra/Por4 dialysis membrane 6 and is eluted into 10 mL vessel 8. The opposing half of the polycarbonate block 7 is connected to a LC pump 3 which has a reservoir 4 of artificial saliva that constantly recirculates across the dialysis membrane 6.

In separate experiments, the composition of example 1 was compared with two aqueous formulations of amlexanox which were mucoadhesive but non-viscous, and viscous but non-mucoadhesive, to demonstrate that both properties are required for optimal drug delivery from a free-flowing liquid formulation.

2.9–3.1 mL of the aqueous formulation of amlexanox is applied to the dialysis membrane of the in vitro system, and the flow of artifical saliva was initiated at a rate of 1.0 mL/min. mL samples were withdrawn from the reservoirs 4 and 6 and samples were assayed for amlexanox content using the HPLC assay described in Example 3.

Figure 3:
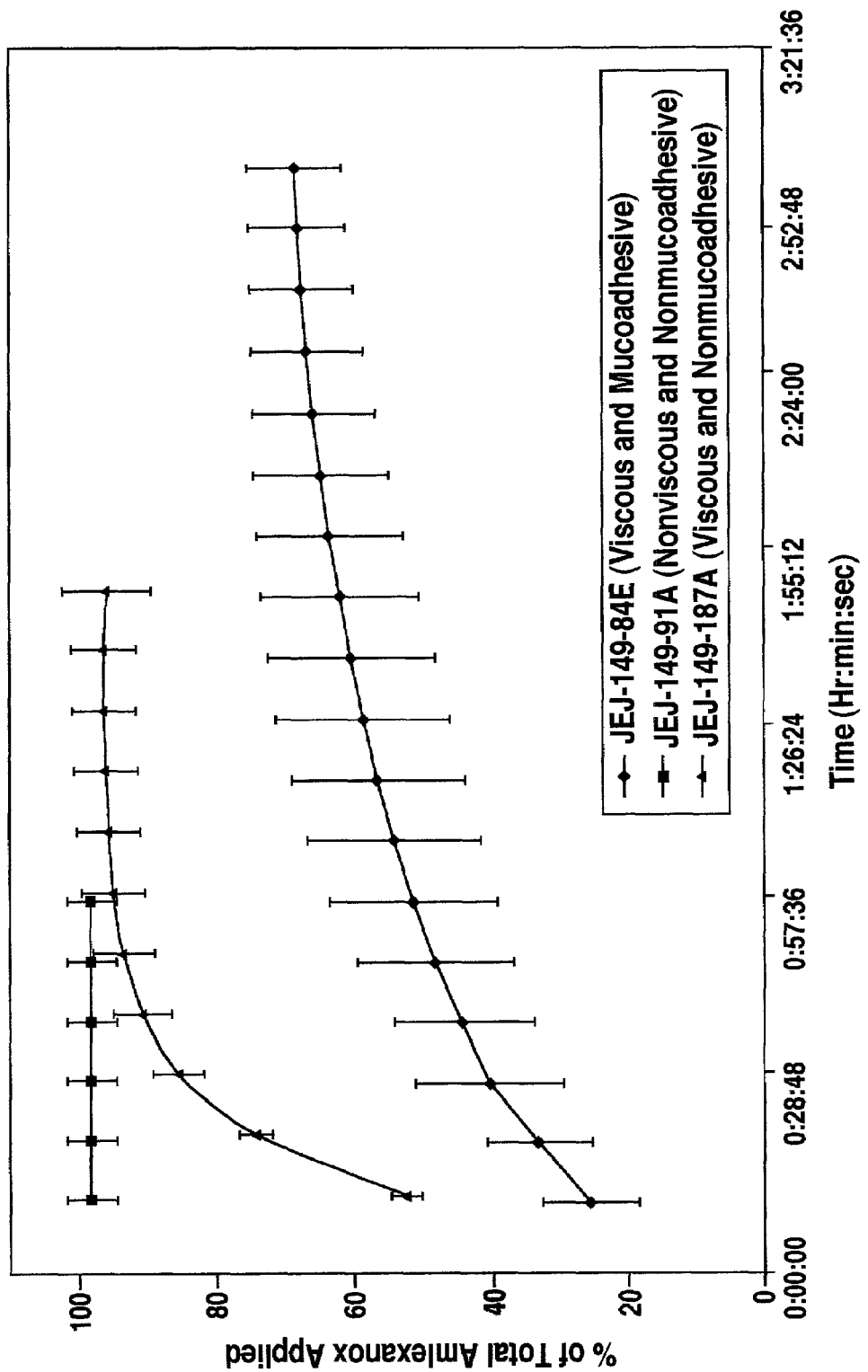
FIGS. 3 and 3a show results of amlexanox delivery of three difference formulations when tested using the device shown in FIGS. 1 and 2.
Figure 3B:
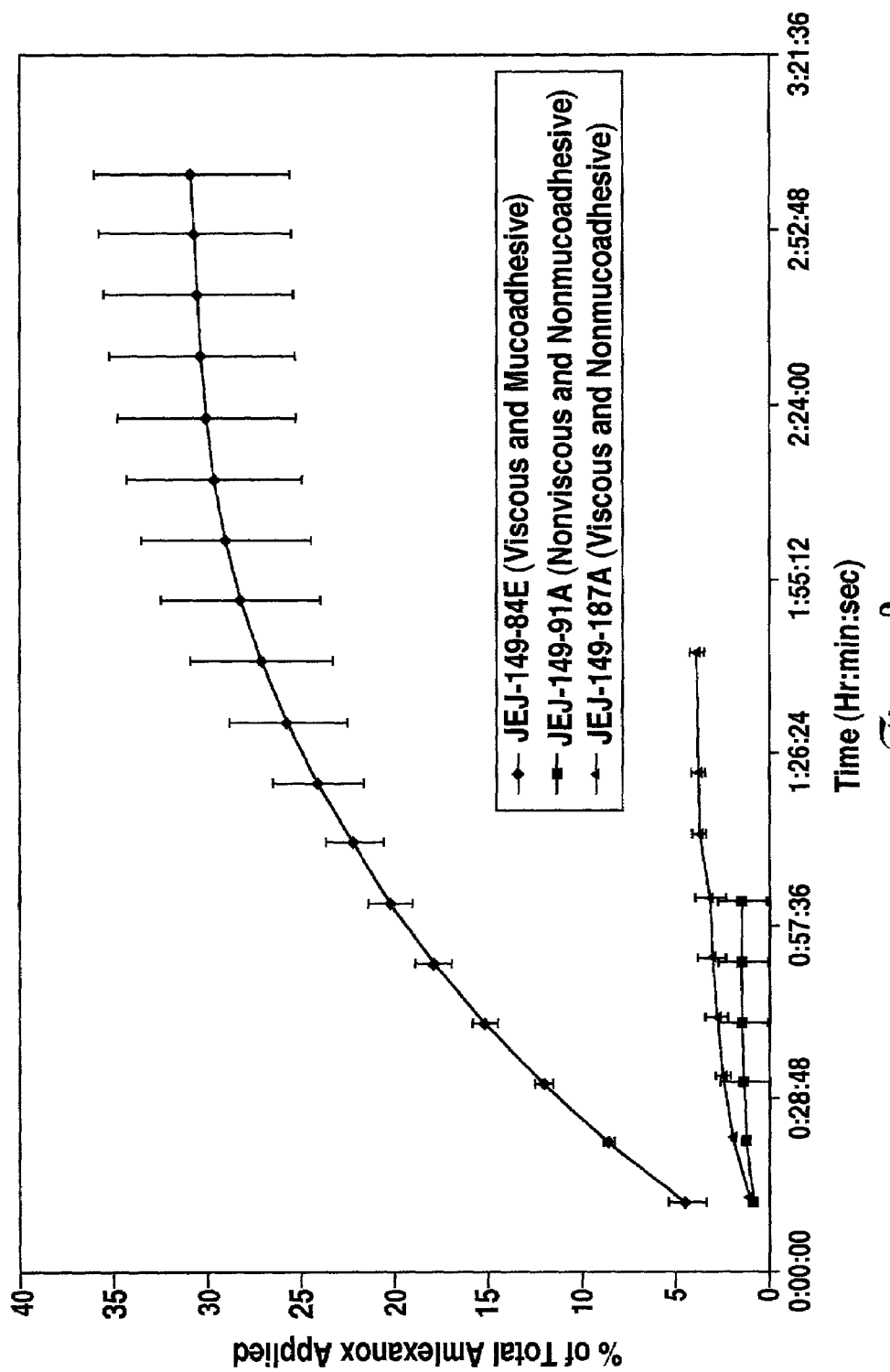

The results of this study are shown in FIG. 3. As can be seen in FIG. 3a, much less amlexanox is washed away in the simulation of saliva flow in the case of the viscous, mucoadhesive solution which is the subject of this invention compared with the other two formulations. As a result, much more amlexanox (the data indicates a ten-fold difference) is delivered to the membrane and transported to the receiver vessel in the case of the viscous, mucoadhesive solution which is the subject of this invention compared with the other two formulations.

Example 5

Stability Study

The composition of example 2 was subjected to a stability study. The clear solution was packaged in clear glass bottles which were sealed with white screw caps fitted with teflon liners. The bottles were divided into two groups. One group was stored in a stabilty chamber set at 25° C./60% relative humidity, while the second group was stored at 40° C./75% relative humidity. Bottles were examined at 0, 1, 2, 3, and 6 months for physical appearance (clarity of the solution), package integrity, amlexanox and benzyl alcohol contents, pH, and viscosity. At all times and under both conditions, no physical or chemical changes were noted.

Example 6

Clinical Study

A clinical study was conducted in patients 18 years of age or older with a histologically documented diagnosis of head-and-neck cancer and a KPS of at least 60%, who received a radiation dose of at least 60 Gy over 6–7 weeks with radiation fields to include at least 40% of the oral mucosa. Patients receiving concomitant chemotherapy were also included in the study. The patients rinsed using the solution exemplified in example 1 for 6 times a day (5 mL each time) for the duration of the radiation treatment (6–7 weeks), beginning on the first day of radiation therapy. An objective measurement of the degree of mucositis (the "Sonis Scale", described in Cancer, 1999, 85(10) 2103–13) was made three times a week for the duration of the study. The following table demonstrates the mean and median scores of patients on days 14, 28, and 39. These data were obtained on 12 subjects. Historical data (Sonis scale mucositis scores for a similar patient population, 17 patients in total, undergoing similar treatment for head-and-neck cancer) are provided for comparison.

TABLE 3

|  | Day 14 | Day 28 | Day 39 |
| --- | --- | --- | --- |
| Median |  |  |  |
| No Treatment | 0.88 | 1.50 | 1.70 |
| Rinse (example 1) | 0.87 | 0.44 | 0.39 |
| Mean |  |  |  |
| No Treatment | 1.01 | 1.50 | 1.62 |
| Rinse (example 1) | 0.44 | 0.81 | 0.85 |

Example 7

Mucoadhesive Gel Formulations

Six gel formulations were prepared similarly using a lightning mixer with an A-100 propeller. For the sample denoted as B detailed below, 354 grams of 50 mM glycine/sodium hydroxide buffer solution were added to a 600 ml beaker and stirred at 200 rpm. The buffer was prepared by combining 1 liter of a 0.2 M aqueous glycine solution with 176 ml of 0.2 N sodium hydroxide solution and 2984 ml deionized water. Fifty grams of 95% USP Ethanol were added next, then 5 grams of glycerin. The stirring speed was increased to 300 rpm, and 5 grams of Noveon AA1 were added slowly to the vortex, and the speed gradually increased to 700 rpm. This solution was homogenized for one hour. Fifty grams of Carbopol® 971P NF were added slowly to the vortex and the speed gradually increased to 1200 rpm. The material was mixed for an additional one half hour, and 75 grams of 2N sodium hydroxide and 5 grams of phenoxyethanol were then added. The resulting gel was mixed for an additional one half hour and the pH measured and found to be 9.82. The mixing speed was reduced to 1000 rpm and the pH adjusted to 9.01 using 6.4 ml of 1N hydrochloric acid. The final gel product was clear, homogeneous and transferred to a polypropylene container.

Example 8.

Rheology study

Figure 5:
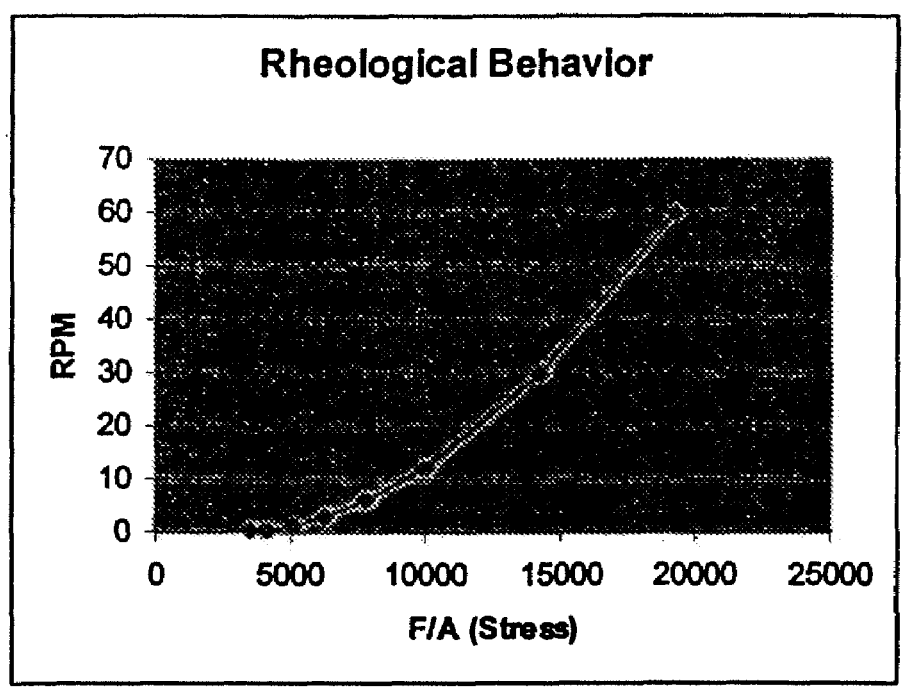
FIG. 5 shows the rheological behavior as measured in Example 8.

A Brookfield viscometer was used to determine the rheological behavior of the oral rinse at 37±1° C. A rheogram was generated by progressively increasing RPM, from 0.3 up to 60 RPM (upcurve) recording the % Torque after each reading stabilized. The upcurve was immediately followed by a downcurve, from 60 RPM to 0.3 RPM. Viscosity is calculated at each RMP, and the stress is then determined by multiplying the viscosity by the RPM. The rheological profile was generated by plotting stress (e.g., F/A) on the x-axis and the RPM (e.g., Rate of Shear) on the y-axis, and this result is presented in FIG. 5.

The rinse is clearly pseudoplastic, yet it does not present any hysteresis. This shear-thinning system has an apparent viscosity that exceeds 10,000 cP at the lowest rate of shear, but that falls to approximately 322 cP at 60 RPM, the highest rate of shear employed.

The above method was used to prepare gels with the following formulations:

TABLE 4

|  | A | B | C | D | E | F |
| --- | --- | --- | --- | --- | --- | --- |
| 50 mM Glycine/NaOH Buffer | 71.5% | 70.8% | 71.8% | 0.0% | 67.0% | 77.9% |
| 100 mM Glycine/NaOH Buffer | 0.0% | 0.0% | 0.0% | 0.0% | 0.0% | 0.0% |
| Boric Acid | 0.0% | 0.0% | 0.0% | 70.8% | 0.0% | 0.0% |
| Glycerin | 1.0% | 1.0% | 1.0% | 1.0% | 1.0% | 0.9% |
| Noveon AA1 | 1.0% | 1.0% | 1.0% | 1.0% | 0.0% | 0.0% |
| Carbomer 971-P | 1.0% | 1.0% | 1.0% | 1.0% | 3.0% | 0.0% |
| Eudragit L100 | 0.1% | 0.0% | 0.0% | 0.0% | 0.0% | 0.0% |
| Ethanol | 10.0% | 10.0% | 10.0% | 10.0% | 10.0% | 9.1% |
| 2N NaOH | 14.4% | 15.2% | 15.2% | 15.2% | 18.0% | 0.0% |
| Phenoxy Ethanol | 1.0% | 1.0% | 0.0% | 1.0% | 1.0% | 0.9% |
| Polyvinyl Alcohol | 0.0% | 0.0% | 0.0% | 0.0% | 0.0% | 10.9% |
| PEG-20,000 | 0.0% | 0.0% | 0.0% | 0.0% | 0.0% | 0.3% |
| Totals | 100% | 100% | 100% | 100% | 100% | 100% |
| PH | 8.8 | 9.01 | 9.00 | 9.00 | 9.00 | 9.01 |
| Viscosity (cP) at 18.3° C. | 8800 | 8200 | 9200 | 7900 | 6900 | 8400 |
| Total mucoadhesive gel % | 2.1% | 2.0% | 2.0% | 2.0% | 3.0% | 0.0% |

Example 9

Hamster Mucositis Study

Figure 4:
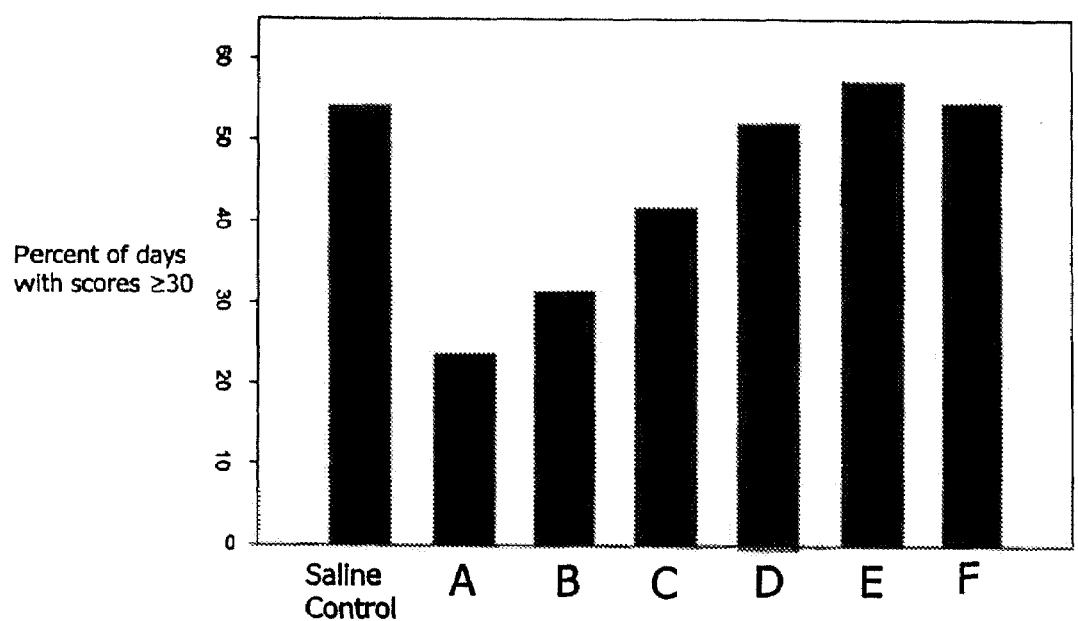
FIG. 4 summarizes the result of a comparison of the formulations described in Example 7.

Fifty-six (56) hamsters were given an acute radiation dose of 40 Gy directed to their oral mucosa on day 0. Test materials (each of the above formulations A–F were applied topically beginning the day before radiation (day −1) and continuing until 20 days following radiation (day 20). The grade of mucositis was scored, beginning on day 6, and for every second day thereafter, until the end of the study on day 28. The effect on mucositis of each treatment group was compared to the saline control. Each animal was scored according to a mucositis scale (0–5) in which 0 represents no mucositis, 5 represents severe mucositis, and a score of three or above indicating that ulceration was observed. The mean of scores of animals in each group was recorded, and the number of days hamsters in each group have severe (score>3) mucositis was calculated. Treatment efficacy was defined as a statistically significant lower number of hamsters with this score in a drug treatment group, versus control as determined by chi-square analysis. FIG. 4 summarizes the result of a comparison of the formulations described in example 9.

Those skilled in the art will recognize that, while specific embodiments and examples have been described, various modifications and changes may be made without departing from the scope and spirit of this invention.

What is claimed is:

1. A pseudoplastic liquid composition for treating or inhibiting an oral mucocutaneous disorder, said pseudoplastic liquid composition having a zero shear viscosity at 37±1 degrees Celsius of 100-20,000 centipoise, comprising 0.1 to 2.0 wt/wt% of one or more mucoadhesives, wherein the mucoadhesive(s) is/are selected from the group consisting of polyvinylpyrrolidone, carboxymethylcellulose, dextran sulfate, hydroxyalkylcellulose, dermatan sulfate, a water-soluble vinyl polymer, chitosan, guar gum, xanthan gum, tragacanth gum, pectin and polyacrylic acid; wherein said pseudoplastic viscous liquid composition, when administered to an oral mucosa:
   1) remains liquid when shear is applied due to swishing the liquid in the mouth; and
   2) attaches to and coats the oral mucosa upon discontinuance of said shear.

2. The pseudoplastic liquid composition of claim 1, wherein the mucoadhesive is cross-linked polyacrylic acid.

3. The pseudoplastic liquid composition of claim 2, wherein the mucoadhesive is selected from the group consisting of carbopol or polycarbophil.

4. The pseudoplastic liquid composition of claim 1, wherein the mucositis is erythema or ulceration induced by chemotherapy or radiation therapy.

5. The pseudoplastic liquid composition of any one of claims 1 or 2, further comprising a preservative with antibacterial activity.

6. The pseudoplastic liquid composition of claim 5, wherein the preservative is selected from the group consisting of methyl parabens, propyl parabens, benzyl alcohol, phenoxyethanol and mixtures thereof.

7. The pseudoplastic liquid composition of any one of claim 1 or 2, further comprising one or more viscosity-inducing agent(s).

8. The pseudoplastic liquid composition of claim 7, wherein the viscosity-inducing agent is selected from the group consisting of an inorganic salt of a monovalent, divalent or trivalent cation.

9. The pseudoplastic liquid composition of claim 8, wherein the inorganic salt is selected from the group consisting of pharmaceutically-acceptable sodium, potassium, calcium, magnesium, zinc or aluminum chloride, bromide, phosphate, borate, tartrate or benzoate.

10. The pseudoplastic liquid composition of claim 7, wherein the viscosity-inducing agent is selected from the group consisting of agar, bentonite, glycerin, povidone, kaolin, tragacanth and sodium alginate.

11. The pseudoplastic liquid composition of any one of claims 1 or 2, further comprising one or more pharmaceutically-acceptable excipients.

12. The pseudoplastic liquid composition of claim 11, wherein the pharmaceutically-acceptable excipient(s) is/are selected from the group consisting of a preservative, a humectant, an emulsifying agent, an antioxidant, an antimicrobial agent, a solubilizing agent, a flavoring agent and a sweetening agent.

13. The pseudoplastic liquid composition of claim 1 wherein the amount of mucoadhesive is 0.35 weight percent.

14. A pseudoplastic liquid composition for treating or inhibiting an oral mucocutaneous disorder, said liquid composition having a zero shear viscosity at 37±1 degrees Celsius of 100-20,000 centipoise, said liquid composition comprising 5% by weight of glycerine, 0.35% by weight of carbopol, 0.35% by weight of potassium hydroxide, and about 1.5% by weight of benzyl alcohol; wherein said viscous liquid composition, when administered to an oral mucosa:
   1) remains liquid when shear is applied due to swishing the liquid in the mouth; and
   2) attaches to and coats the oral mucosa upon discontinuance of said shear.

15. A pseudoplastic liquid composition of claim 1, 13 or 14, wherein the composition provides a mean Son is scale rating of less than 1 when contacted with the oral mucosa of a subject suffering from mucositis.

16. The pseudoplastic liquid composition of claim 15, wherein the subject suffering from mucositis is a cancer patient undergoing cancer therapy.

* * * * *